United States Patent [19]

Logan

[11] Patent Number: 5,050,614

[45] Date of Patent: Sep. 24, 1991

[54] APPARATUS AND METHOD FOR INSPIRATION DETECTION

[75] Inventor: Charles H. Logan, Woodinville, Wash.

[73] Assignee: SpaceLabs, Inc., Redmond, Wash.

[21] Appl. No.: 893,835

[22] Filed: Aug. 6, 1986

[51] Int. Cl.$^5$ .............................................. A61B 5/08
[52] U.S. Cl. ..................................... 128/716; 178/723
[58] Field of Search ........................ 128/716, 723, 725

[56] References Cited

U.S. PATENT DOCUMENTS

| | | |
|---|---|---|
| 4,305,400 | 12/1981 | Logan. |
| 4,444,201 | 4/1984 | Itoh .................................... 128/716 |
| 4,475,558 | 10/1984 | Brock .................................. 128/716 |
| 4,580,575 | 4/1966 | Birnbaum ........................... 128/716 |

Primary Examiner—Kyle L. Howell
Assistant Examiner—J. Hanley
Attorney, Agent, or Firm—Seed and Berry

[57] ABSTRACT

An apparatus and method for detecting patient inspiration is provided. It includes means for providing a baseline level for the patient's respiration signal and for establishing a trigger level representative of inspiration. When the respiration signal crosses the trigger level for selected crossovers inspiration trigger signals are generated. Most importantly means are provided for automatically detecting shifts in the baseline level and for re-establishing the trigger level for the shifted waveform. In the preferred embodiment the apparatus is capable of detecting a baseline shift in about one cycle of the respiration waveform.

The apparatus and method further provides for an inspiration detector with adjustable detection characteristics to accommodate both adult and neonate patients.

26 Claims, 4 Drawing Sheets

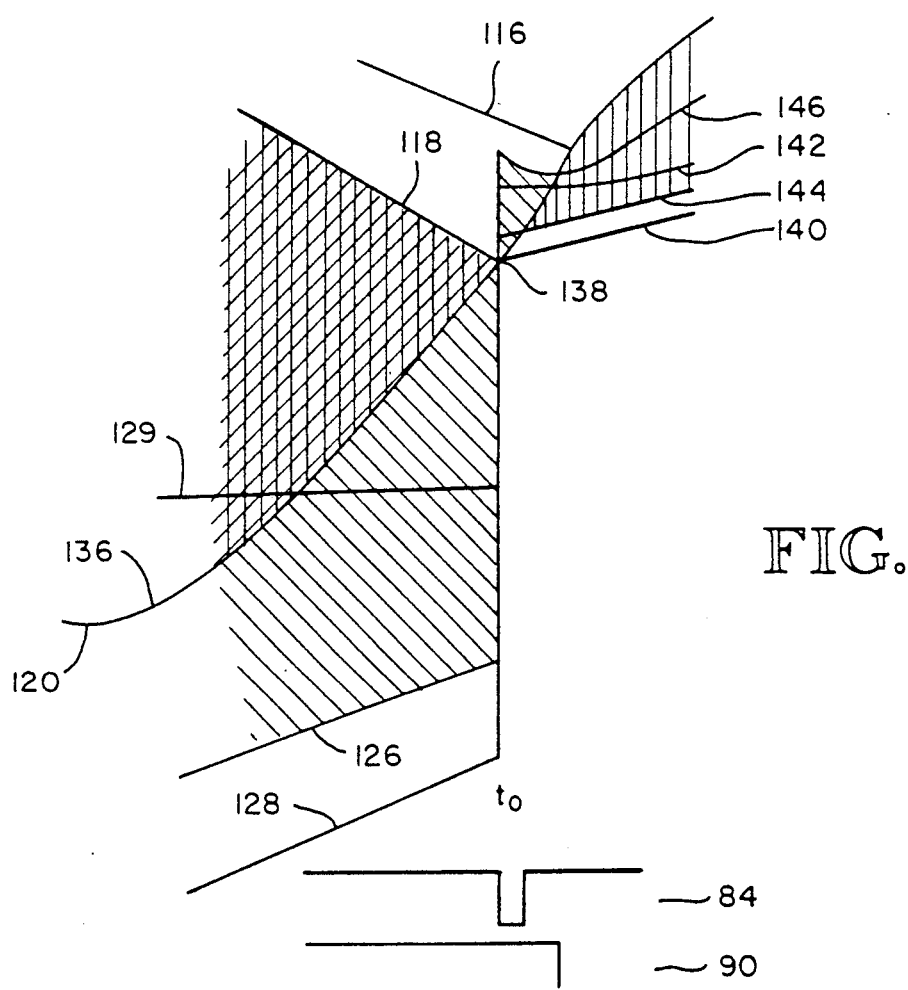

APPARATUS AND METHOD FOR INSPIRATION DETECTION

BACKGROUND OF THE INVENTION

The present invention relates to an apparatus and method for detecting the inspirations of a patient.

In monitoring a patient, it is desirable to detect and measure the rate of inspiration of the patient, inspiration being the act of drawing air into the lungs. Prior art devices do this by establishing a baseline level for the time varying bipolar respiration signal which level falls between (usually midway between) the peak to peak variations of the respiration signal. A trigger level, a predetermined amount above the baseline level, is established and selected ones of the positive crossovers are chosen as inspiration events.

Usually prior art devices include a cardiovascular detector for detecting the presence of cardiovascular artifact (CVA, a low level time varying signal which is created by the pumping action of the heart into the thoracic-cavity) and inhibiting the output of inspiration trigger signals when it is suspected that the inspiration detector is detecting CVA and not inspiration.

Also, prior art devices will only generate an inspiration signal if the respiration signal remains positive for a predetermined amount of time after a positive crossover of a trigger level.

Sometimes due to patient movement, for example, there will be a sudden shift up or down of the dc level of the respiration waveform which will cause the inspiration detector to lose track of the signal and miss valid inspiration events. Prior art devices are not equipped to detect baseline shifts in a timely manner, e.g. within a respiration cycle or two of the shift. It is desirable in adults and particularly in neonates to react quickly to sudden baseline shifts in the respiration signal, and to be able to accommodate both adult and neonate inspiration detection characteristics like CVA, qualifier time and baseline and trigger level calculations in the same apparatus.

SUMMARY OF THE INVENTION

An apparatus and method for detecting patient inspiration is provided. It includes means for providing a baseline level for the patient's respiration signal and for establishing a trigger level representative of inspiration. When the respiration signal crosses the trigger level for selected crossovers inspiration trigger signals are generated. Most importantly means are provided for automatically detecting shifts in the baseline level and for re-establishing the trigger level for the shifted waveform. In the preferred embodiment the apparatus is capable of detecting a baseline shift in about one cycle of the respiration waveform.

In the preferred embodiment the means for automatically detecting a baseline shift includes establishing adjacent sector boundaries of opposite polarity for each cycle of the respiration waveform and detecting when the waveform crosses a sector boundary of a first polarity at least two times in succession without crossing the sector boundary of opposite polarity.

The apparatus and method further provides for an inspiration detector with adjustable detection characteristics to accommodate both adult and neonate patients.

BRIEF DESCRIPTION OF THE DRAWINGS

FIG. 5 is an enlarged graphic representation of a portion of the waveform of FIG. 4 at the point where the baseline shift is detected and the baseline reset.

DETAILED DESCRIPTION OF THE DRAWINGS

Figure 1:
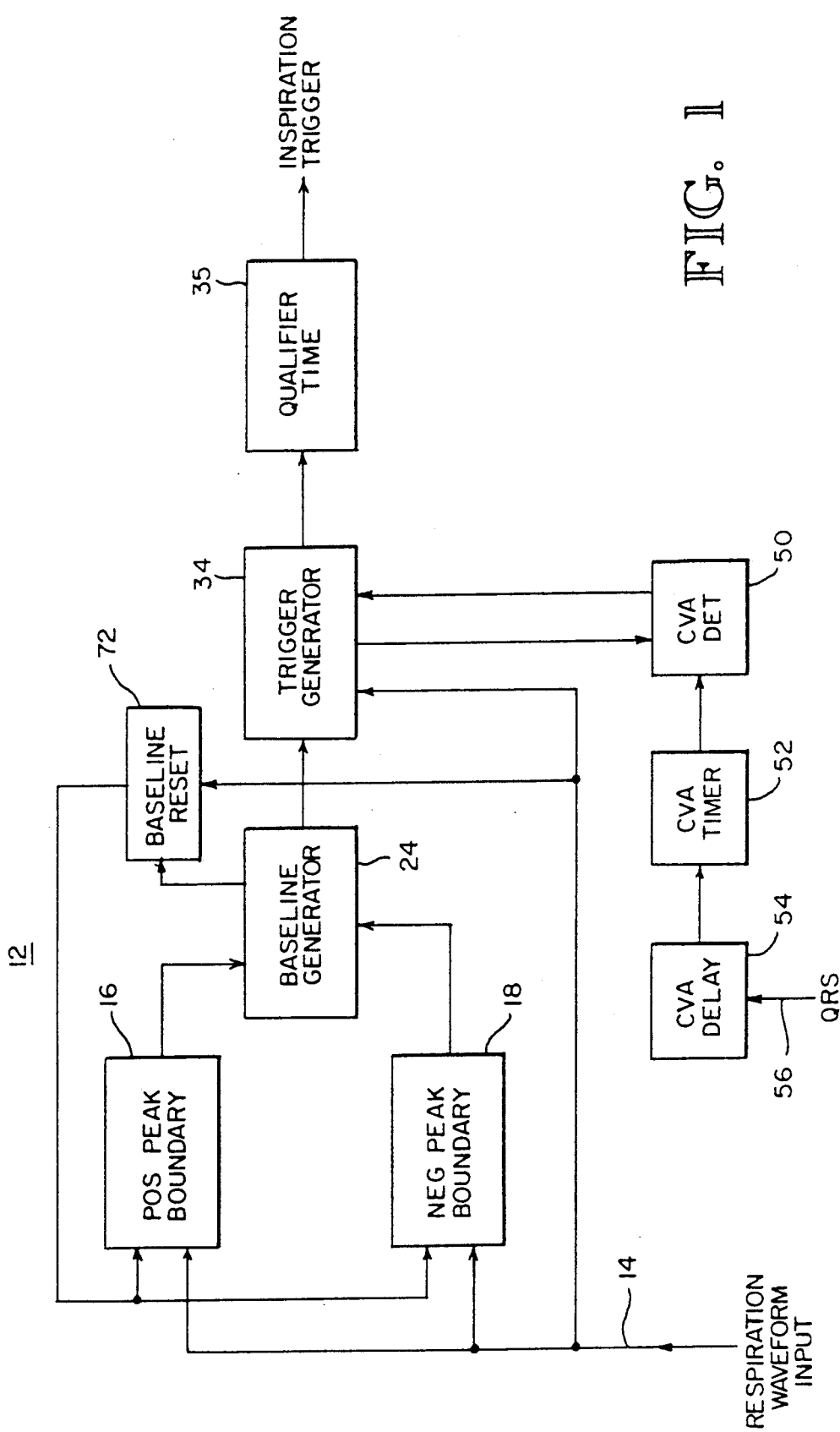
FIG. 1 is a block diagram of computer program modules of the preferred embodiment inspiration detector.
Figure 2:
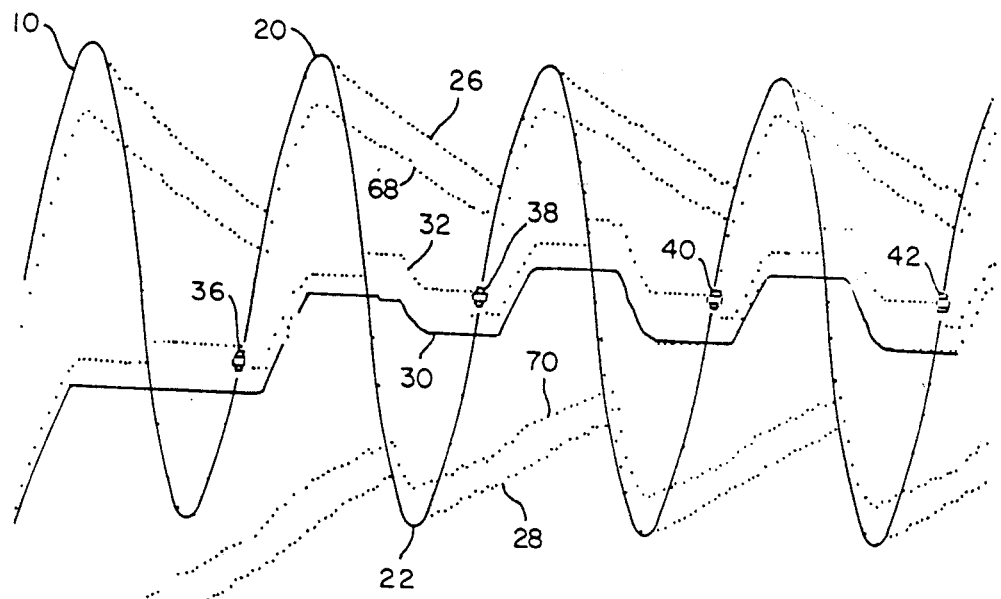
FIG. 2 is a graphic representation of the respiration signals and related parameters important to the practice of the present invention inspiration detector.

Referring now to the FIGS., the respiration signal, represented by the sinusoidal waveform 10 in FIG. 2, is provided by respiration detection circuitry and digitized. It is provided to the inspiration detector designated generally 12 in FIG. 1 along the 8 bit bus 14. The inspiration detector 12 includes positive and negative peak boundary generation means 16 and 18, respectively, for detecting the positive and negative peaks 20 and 22, respectively, and for generating positive and negative peak boundaries in the following way.

A positive peak decay and a negative peak decay are applied to each peak detected. The decay is a slow exponential decay of the peak amplitude with time designed to intersect the respiration waveform on the next rise or fall to the following positive or negative peak. The peak decay from the peak until its intersection with the waveform defines the positive peak boundary 26 and the negative peak boundary 28. The peak detection and generation of the peak boundaries is described in P code at the bottom of page 15 and the top of page 16. The separation between the positive and negative peak boundaries is constantly checked to see that it is above a predetermined minimum separation. See the "test peak boundaries" portion of the P-code at page 16. The baseline 30 is defined as the halfway point on a sample by sample basis between the positive and negative peak boundaries 26 and 28, respectively. See the "adjust the baseline" portion of the P-code on page 15.

Following generation of the baseline 30, the trigger level 32 is established and trigger signals to indicate inspiration are generated by the trigger generator 34 in FIG. 1 The trigger level 32 equals the baseline value 30 plus a predetermined minimum threshold level minus a threshold modifier. In the preferred embodiment the threshold modifier equals the positive peak boundary value minus the negative peak boundary value, the difference divided by 8. The minimum threshold depends on whether a normal or shallow threshold is selected by the operator who makes the selection depending on whether the patient has a deep respiration pattern (normal) or a shallow respiration pattern (shallow). Where the normal threshold has been selected, minimum threshold equals a predetermined shallow threshold value plus a preset increased threshold value. If the operator selects a shallow threshold then the minimum threshold equals the shallow threshold. The threshold level 32 is therefore determined by the operator and is a function of the peak to peak value for the respiration signal on a sample by sample basis. "Calculate the inspiration trigger threshold modifier" and "calculate the inspiration trigger threshold" portions of the P-code are on pages 13 and 14.

The trigger generator 34 checks to see when the input signal crosses the trigger level in both the positive and negative directions. Each time the input crosses the trigger level 32, the trigger generator generates a positive edge trigger signal of one sample time duration and a negative edge trigger signal of one sample duration. It also produces an old inspiration trigger signal for the duration that the input remains above the threshold level 32. See the "check the input to see if trigger criteria are met" portion of the P-code on page 14. Inspiration trigger signals are only generated in response to positive direction crossovers such as at the crossovers 36, 38, 40 and 42 in FIG. 2 and then only when other criteria to be described below are met.

Before the positive going trigger level crossings can be counted as detected inspiration events, the system must check for the presence of cardiovascular artifact (CVA). CVA is caused by the change in impedance in the thorax caused when a bolus of blood fills the thoracic cavity after each heartbeat. It is repetitive and usually a negative signal, although in small babies (neonates) it can be positive since the baby's heart is a larger part of the thoracic cavity. If CVA is present and no respiration is present, an inspiration detector could be fooled into counting the CVA as inspiration.

Baseline crossings by the CVA induced signal are time correlated with the QRS signal from the heartbeat. The CVA detector 50 of the present invention looks to see if any positive or negative edge triggers from the trigger generator 34 fall within a CVA window 52 of predetermined duration occurring a preset time delay 54 from the presence of a QRS signal furnished on line 56 by an ECG detector external to the inspiration detector. The CVA detector 50 then compares the heart rate based on the QRS signals with the respiration rate. If they are within 12.5% of each other and a positive or negative trigger occurred within the CVA window 52, then the CVA detector accumulates an increment of a predetermined value. Each time either a positive or a negative edge trigger is generated outside the CVA window, the CVA detector accumulates a decrement of twice the predetermined value. If, during any 10-second period, the CVA detector repetitively accumulates increments without any decrements, the inspiration detector output will be inhibited. The CVA detector, timer and delay are implemented in P-code at pages 14 and 15 of the P-code. Two thimbles are emptied from the bucket each time there is a QRS signal without an associated co-incident inspiration positive or negative edge trigger. The 12.5% comparison done in P-code at page 16, insures that detection of inspiration will not be inhibited in the event of respiration at a much slower rate than the heartrate and somewhat synchronized therewith, which occurs sometimes in small babies for ten seconds duration or so.

Negative and positive sector boundaries 68 and 70, respectively, are generated by the baseline reset means 72. The positive sector boundary 68 is equal to the baseline value minus the negative peak boundary value, the difference being multipled by a fraction, the positive boundary percentage. This value is added to the negative peak boundary to define the positive sector boundary 68 on a sample by sample basis. Similarly, the negative sector boundary 70 is formed by subtracting the baseline value from the positive peak boundary value, the difference being multiplied by a fraction, the negative boundary percentage. This value is subtracted from the positive peak boundary to form the negative sector boundary on a sample by sample basis. See the P-code at the bottom of page 16 and the top of page 17.

Figure 3:
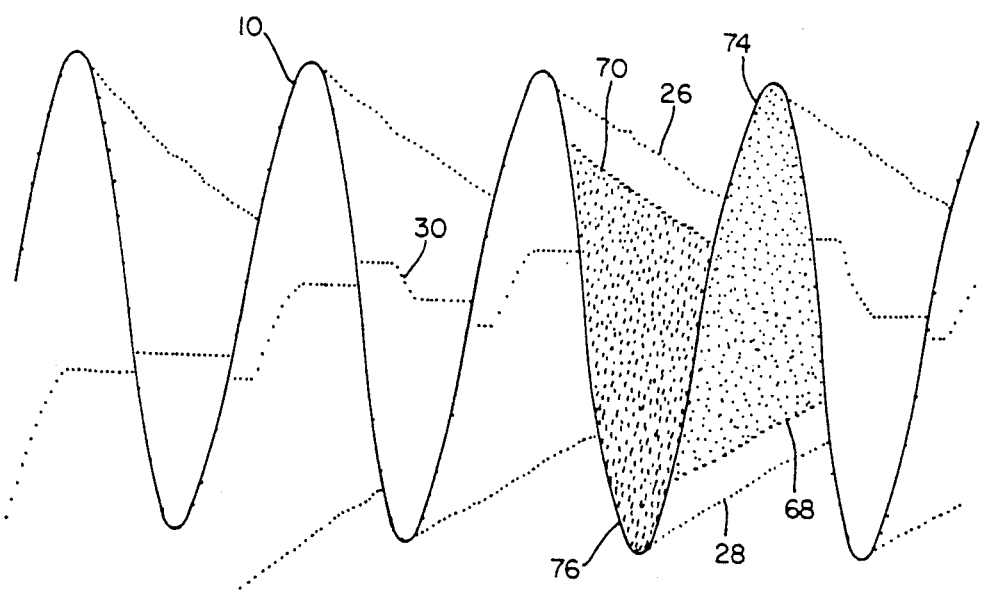
FIG. 3 is a graphic representation of positive and negative sectors of the respiration waveform.

The sector boundaries just described are used to form positive and negative waveform sectors 74 and 76, respectively, which are shown more clearly in FIG. 3 along with the respiration signal 10, the positive peak boundary 26, the negative peak boundary 28 the baseline 30, the negative sector boundary 70, and the positive sector boundary 68. The negative sector 76 is formed by the negative sector boundary and the waveform portion defined by the intersection of the waveform with the negative sector boundary on either side of the negative peak, while the positive sector 74 is formed by the positive sector boundary 68 and the waveform portion defined by the intersection of the waveform with the positive sector boundary 68 on either side of the positive peak.

Figure 4:
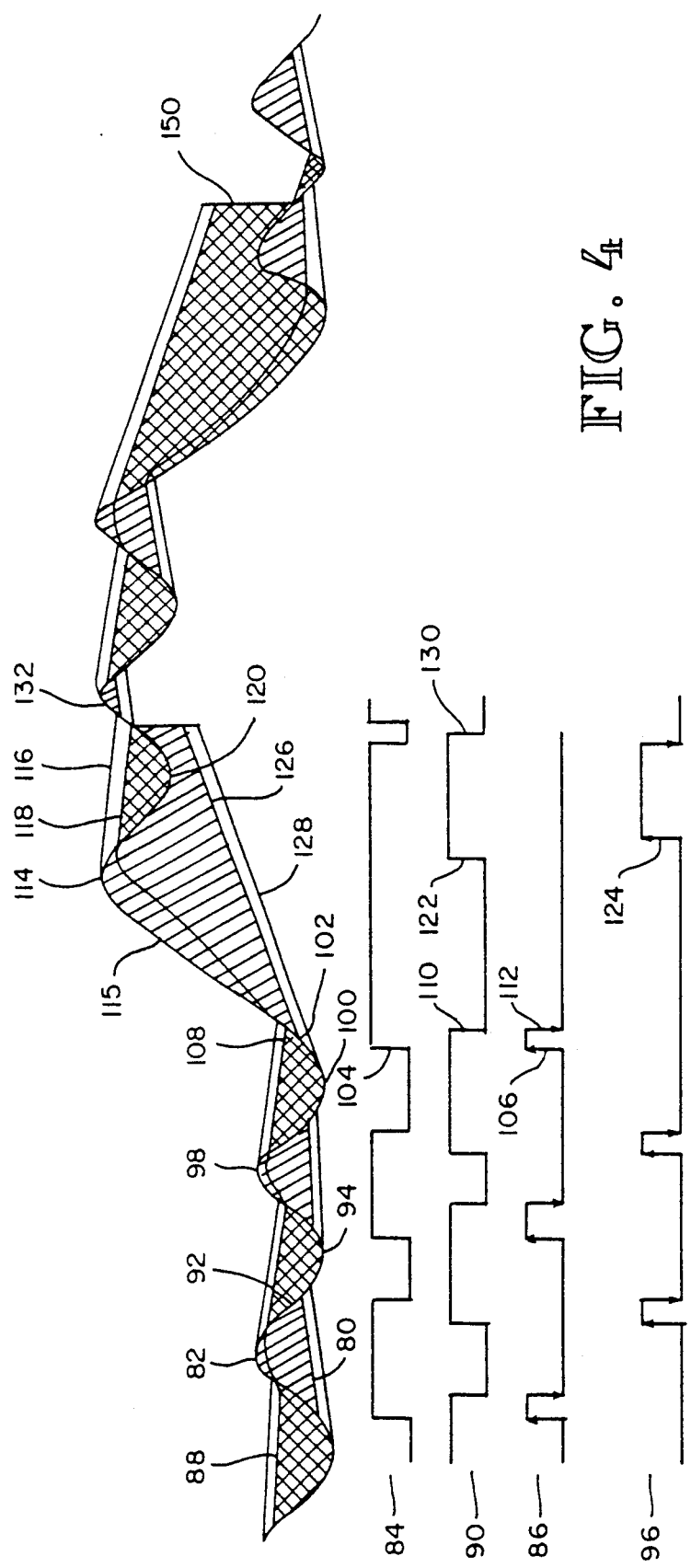
FIG. 4 is graphic representation of detection of a sudden shift in the respiration waveform baseline and the re-setting of the baseline.

The sector boundaries 68 and 70 are formed to aid in resetting the baseline when there is a radical shift up or down in the dc level of the respiration waveform due to patient movement, for example. FIG. 4 shows a respiration waveform which is first at one baseline level and then moves upward on the FIG. radically to a second much higher baseline and then returns to the first baseline level. Prior art systems not equipped with the sector boundaries 68 and 70 and the baseline reset means 72 of the invention, would most likely loose track of the respiration signal for a relatively long period of time (several seconds or so) and would require re-initialization of the system to acquire tracking of the signal.

Referring now to FIGS. 4 and 5 and the P-code listing on page 13 as the input waveform passes through the positive sector boundary 80 as it approaches the first positive peak 82, the positive sector active flag 84 is set true. At the same time the positive peak reset flag 86 is set true. The input as it continues to rise passes out of the negative sector past the negative sector boundary 88 associated with the previous negative peak and the negative sector active flag 90 goes false along with the positive peak reset flag 86. The input will pass the positive peak 82, cross the negative sector boundary 92 for the next upcoming negative peak 94 causing the negative sector active flag 90 to go high again. At the same time the negative peak reset flag 96 is set true. When the input passes the positive sector boundary 80 on its way to the negative peak 94 the positive sector active signal flag 84 is set false along with the negative peak reset flag 96. The same series of events is repeated as the input passes through the positive peak 98 on its way to the following negative peak 100. To summarize, each time the input passes into a new waveform sector it sets the sector active and peak reset armed flags true for that sector. For well behaved waveform, just after passing into a new sector, the input will pass out of an old sector causing that sector's sector active flag to go false and setting the new sector's peak reset armed flag back to false.

Following the input through negative peak 100, as the waveform passes through the positive sector boundary 102 the positive sector active flag 84 goes true at 104 along with the positive peak reset armed flag at 106. Soon after this the input crosses the negative sector boundary 108 for the prior negative sector causing the negative sector active flag 90 to go false at 110 and set the positive peak reset armed flag 86 false at 112. At this point a major shift in the dc level of the waveform occurs (possibly due to patient movement) and the input continues to increase to the much higher positive peak 114 along the curve 115. The positive peak boundary 116 and the negative sector boundary 118 will follow the input and as the input enters the negative sector for negative peak 120 the negative sector active signal 90 goes true at 122 as does the negative peak reset armed flag 96 at 124. The input never crosses the positive peak sector boundary 126 which has been following the negative peak boundary 128 decaying from the previous negative peak 100 so the negative peak reset armed flag 90 is not set false. When the input passes through negative peak 120 and then the negative sector boundary 118, the negative sector active signal goes false at 130, and the negative peak reset armed signal is checked to see if it is true or false. If it is still true then the baseline reset means 72 knows that the input passed through a positive sector (for peak 114) and back again to another positive sector 132 without passing through a negative sector boundary (126). Therefore, it is time to reset the baseline. See the P-code at page 13.

FIG. 5 shows what happens to the various boundaries and baseline at the point when the baseline reset takes place. Prior to time $t_o$, the reset time, the negative peak boundary 128 and the positive sector boundary 126 were decaying from prior negative peak 100 at the lower baseline. They do not intersect the waveform 136 at the negative peak 120. The positive peak boundary 116 and negative sector boundary 118 are behaving normally. At time $t_o$, the negative peak boundary is reset to the input 136 at 138 to form the new negative peak boundary 140. A new baseline 142 is recalculated from the positive and negative peak boundaries 116 and 140, respectively, and then new positive and negative sector boundaries 144 and 146 are also recalculated as described earlier. The positive sector active flag 84 is set false and the negative sector active flag is set true. At this point the system has automatically reset the baseline and is again tracking the inspiration signal.

FIG. 4 further shows the respiration signal falling after a couple of cycles from the new baseline back to the old baseline. The system at point 150 automatically resets as described above but for the opposite polarity.

At the time that a positive edge trigger signal is generated by the trigger generator it will be remembered that a flag called old inspiration trigger is set true. At the same time a flag called positive trigger time is set equal to the system time, which is a continuous running clock which counts milliseconds of operation of the system from the power up time. If while the old inspiration trigger flag remains true, the system time minus the positive trigger time becomes greater than or equal to a qualifier time 35, then the inspiration detector 12 will generate an inspiration trigger signal. The qualifier time is greater for an adult then for a neonate and is preset in the system.

At power on, or during operation, the operator tells the detector 12 whether the patient is an adult or neonate. The detector automatically adjusts the threshold, peak decay rates and qualifier time in response thereto.

INSPIRATION DETECTOR P-CODE

```
set_insp_variables:

select resp_page in external ram
put positive_peak_boundary from last calculation into R7
put negative_peak_boundary from last calculation into R6
put baseline from last calculation into R5

/* check to see if the last ERS interrupt set e_t_b to TRUE */ if (empty_the_bucket := TRUE) then
    empty_the_bucket = FALSE
    thimble = EMPTY
fi /* check for lead fault or trace recover in action */ if ((resp lead fault | resp trace recover) = TRUE) then
    positive_peak_boundary = 80H    /* 80H is center screen */
    negative_peak_boundary = 80H
    call test_peak_boundaries       /* provide minimum separation */
    baseline = 80H
    baseline filter = 80H
    GOTO exit
fi ;set the cva variables according to the age group passed
        ;from the 'ISR . if (age_group = ADULT) then
    cva_window = ADULT_WINDOW
```

```
   cva_delay = ADULT_DELAY
   qualifier = ADULT_QUALIFIER_TIME
   insp_pass_count_value = ADULT_PASS_COUNT_VALUE
else
   cva_window = NEONATE_WINDOW
   cva_delay = NEONATE_DELAY
   qualifier = NEONATE_QUALIFIER_TIME
   insp_pass_count_value = NEO_PASS_COUNT_VALUE
fi /* process the pass counter for the decay routines */ resp_pass_count += 1
if (resp_pass_count > INSP_PASS_COUNT_VALUE) then
   resp_pass_count = 0
fi ;set the minumum_threshold according to shallow/normal
       ;sensitivity sent from the 'ISS if (insp_sensitivity = NORMAL) then
   minimum_threshold = SHALLOW_THRESHOLD + INCREASED_THRESHOLD
else
   minimum_threshold = SHALLOW_THRESHOLD
       ;check    put data against the sector boundaries if (positive_sector_boundary -      /* if the sectors are too close */
       negative_sector_boundary -   /* together, don't process them */
       SECTOR_BOUNDARY_SEPARATION
       > 0) then if (input >= positive_sector_boundary) then
      if (positive_sector_active = FALSE) then
         positive_sector_active = TRUE    /* positive sector has just */
         positive_peak_reset_armed = TRUE /* gone active */
      fi
   else   /* input is below the positive_sector_boundary */
      if (positive_sector_active = TRUE) then /* p_s_a has just gone */
         positive_sector_active = FALSE       /* inactive */
         negative_peak_reset_armed = FALSE
         if (positive_peak_reset_armed = TRUE) then /* time to recover */
            positive_peak_reset_armed = FALSE
            positive_sector_active = TRUE
            negative_sector_active = FALSE
            positive_peak_boundary = input
            call test_peak_boundaries
            baseline = (positive_peak_boundary +
               negative_peak_boundary) / 2
            baseline_filter = baseline
            call adjust_positive_sector_boundary
            call adjust_negative_sector_boundary
         fi
      fi
   fi if (input < negative_sector_boundary) then
      if (negative_sector_active = FALSE) then /* negative sector has */
         negative_sector_active = TRUE        /* just gone active */
```

```
            negative_peak_reset_armed = TRUE
      fi
   else    /* input is above the negative_sector_boundary */
      if (negative_sector_active = TRUE) then  /* negative sector has */
         negative_sector_active = FALSE    /* just gone inactive */
         positive_peak_reset_armed = FALSE
         if (negative_peak_reset_armed = TRUE) then /* time to reset */
            negative_peak_reset_armed = FALSE    /* the n_p_b */
            positive_sector_active = FALSE
            negative_sector_active = TRUE
            negative_peak_boundary = input
            call test_peak_boundaries
            baseline = (positive_peak_boundary + negative_peak_boundary) / 2
            baseline filter = baseline
            call adjust_positive_sector_boundary
            call adjust_negative_sector_boundary
         fi
      fi
   fi
else    /* sector boundaries close enough together to skip processing */
   positive_sector_active = TRUE
   negative_sector_actove = TRUE
   positive_peak_reset_armed = FALSE
   negative_peak_reset_armed = FALSE
fi ;calculate the inspiration trigger threshold modifier threshold modifier =
   (positiv    boundary - negative_peak_boundary) / 8

;calculate the inspiration trigger threshold insp_threshold =
   (baseline + minimum_threshold - threshold modifier)
if insp_threshold overflows then
   insp_threshold = positive_peak_boundary
fi
if insp_threshold underflows then
   insp_threshold = negative_peak_boundary
fi /* now check the input to see if trigger criteria are met */ if (input )= insp_threshold) then
   negative_edge_trigger = FALSE
   if (old_insp_trigger = FALSE) then /* threshold just crossed */
      positive_trigger_time = system time
      old_insp_trigger = TRUE
      positive_edge_trigger = TRUE
      insp_has_triggered = FALSE
   else                               /* threshold crossed earlier */
      positive_edge_trigger = FALSE
   fi
else                                  /* input below threshold */
   positive_edge_trigger = FALSE
   if (old_insp_trigger = TRUE) then /* threshold just crossed */
      negative_trigger_time = system time
```

```
         old_insp_trigger = FALSE
         negative_edge_trigger = TRUE
      else
         negative_edge_trigger = FALSE
      fi
   fi ;test to see if the cva rejection feature is enabled if (cva_enable = TRUE) then ;check positive trigger info to test for cva present if (positive_edge_trigger = TRUE) then
      delta_time = (positive_trigger_time - qrs_trigger_time - cva_delay)
      if (delta_time > 0) then          /* trigger after cva_delay */
         delta_time = cva_window - delta_time
         if (delta_time < 0) then       /* trigger within cva_window */
            pos_trig_last_window = FALSE
            positive cva = TRUE
            call compare_rates  /* returns TRUE if hr and rr compare */
                                /* within 12.5 percent */
            if (compare_rates = TRUE) then
               thimble = FILL
            else
               GOTO adjust_bucket
            fi
         else
            GOTO positive_trigger_outside_window
         fi
      else                              /* trigger outside window */
positive_trigger_outside_window:
         positive cva = FALSE
         if (negative cva = FALSE) then
            thimble = EMPTY
         fi
         goto adjust_bucket
      fi
   fi ;check negative trigger info to test for cva present if (negative_edge_trigger = TRUE) then
      delta_time = (negative_trigger_time - qrs_trigger_time - cva_delay)
      if (delta_time > 0) then          /* trigger after cva_delay */
         delta_time = cva_window - delta_time
         if (delta_time < 0) then       /* trigger within cva_window */
            negative cva = TRUE
            neg_trig_last_window = FALSE
            call compare_rates
            if (compare_rates = TRUE) then
               thimble = FILL
            else
               GOTO adjust_bucket
            fi
         else
            GOTO negative_trigger_outside_window
```

```
            fi
         else
negative_trigger_outside_window:
            negative cva = FALSE
            if (positive cva = FALSE) then
               thisble = EMPTY
            fi
            GOTO adjust_bucket
         fi
      fi
   else         /* cva is not enabled */
      insp_trigger_inhibit = FALSE
      thisble = 0
      bucket = 0
      positive cva = FALSE
      negative cva = FALSE
      pos_trig_last_window = FALSE
      neg_trig_last_window = FALSE
      GOTO adjust_baseline
   fi adjust_bucket:
bucket = thisble + bucket
insp_trigger_inhibit = FALSE
if (bucket overflows) then
   insp_trigger_inhibit = TRUE
   bucket = bucket - thisble / 2
fi
if (bucket underflows) then
   bucket = 0
fi ;now adjust the baseline baseline filter input =
   (positive_peak_boundary + negative_peak_boundary) / 2
base_sum = base_sum + (baseline filter input - baseline)
baseline = base_sum / 256

;now use the input data to adjust the peak boundary trackers if (input < positive_peak_boundary) then
   if (resp_pass_count = 0) then
      positive_peak_boundary = baseline +
         POSITIVE_PEAK_DECAY * (positive_peak_boundary - baseline)
      call test_peak_boundaries
   fi
else
   positive_peak_boundary = input
   call test_peak_boundaries
fi if (input > negative_peak_boundary) then
   if (resp_pass_count = 0) then
      negative_peak_boundary = baseline -
         NEGATIVE_PEAK_DECAY * (baseline - negative_peak_boundary)
      call test_peak_boundaries
   fi
```

```
   else
      negative_peak_boundary = input
      call test_peak_boundaries
   fi ;use the peak and baseline numbers to adjust the sector boundaries call adjust_positive_sector_boundary
   call adjust_negative_sector_boundary ;now check to see if it's time to declare an insp trigger if (old_insp_trigger = TRUE) then
      if (insp_has_triggered = FALSE) then
         if (insp_trigger_inhibit = FALSE) then
            if ((sys_time - positive_trigger_time) >= qualifier) then
               insp_has_triggered = TRUE
               call rr_timer    ;/! send trigger flag and time to 'ISS 1/
            fe,
         fi,
      fo,
   fum!

exit:
set external ram to page zero
return to background loop test_peak_boundaries:

if (positive_peak_boundary -
      negative_peak_boundary - PEAK_BOUNDARY_SEPARATION < 0) then
      positive_peak_boundary = negative_peak_boundary +
         PEAK_BOUNDARY_SEPARATION
      if (positive_peak_boundary overflows) then
         positive_peak_boundary = 0FFH
      fi
   fi
return adjust_positive_sector_boundary:

if (baseline - negative_peak_boundary) < 0 then
      positive_sector_boundary = negative_peak_boundary
   else
      positive_sector_boundary =
         (baseline - negative_peak_boundary) *
         POSITIVE_BOUNDARY_PERCENTAGE +
         negative_peak_boundary
   fi
return
adjust_negative_sector_boundary:

if (positive_peak_boundary - baseline) < 0 then
```

```
            negative_sector_boundary = positive_peak_boundary
        else
            negative_sector_boundary =
                positive_peak_boundary -
                (positive_peak_boundary - baseline) *
                NEGATIVE_BOUNDARY_PERCENTAGE
        fi
    return ;compare_rates returns carry = true if the heart rate and resp
    ;rate compare within 12.5 percent.

compare_rates:

if (hr_value < 2048) then       /* if the heart rate is above 29 bpm */
        percentage_factor = hr_value / 8
        upper_hr_bound = hr_value + percentage_factor
        lower_hr_bound = hr_value - percentage_factor
        delta_rate = rr_value - lower_hr_bound
        if (delta_rate > 0) then
            delta_rate = rr_value - upper_hr_bound
            if (delta_rate < 0) then
                compare_rates = TRUE
                return
            fi
        fi
    fi
    compare_rates = FALSE
    return
```

What is claimed is:

1. An apparatus for detecting inspiration of a patient in response to a time varying signal representative of the patient's respiration comprising:
   means for establishing a baseline level for said respiration signal which falls between the peak to peak variations of said respiration signal;
   means for establishing a trigger level for said respiration signal representative of inspiration;
   means for generating inspiration trigger signals in response to selected crossovers of said trigger level by said respiration signal;
   means for automatically detecting shifts in the baseline level of said respiration signal; and
   means responsive to said baseline shift detection means for re-establishing said baseline and trigger levels.

2. The apparatus of claim 1 wherein said baseline shift detection means comprises:
   means for detecting said baseline shifts within approximately one complete cycle of said respiration signal after said baseline shift has occurred.

3. The apparatus of claim 1 wherein said baseline shift detection means comprises:
   means for establishing adjacent sector boundaries of opposite polarity for each cycle of said respiration waveform; and
   means for detecting when said waveform crosses a sector boundary of a first one of said polarities at least two times in succession without passing the sector boundary of the opposite polarity in between.

4. The apparatus of claim 1 wherein said baseline level establishing means comprises:
   means for forming peak boundaries of opposite polarity for said respiration signals which peak boundaries start at each peak of said respiration signal and decay at a predetermined rate until said peak boundary intercepts said waveform before an adjacent peak of the same polarity; and
   means for establishing said baseline level at a level between said peak boundaries of opposite polarity.

5. The apparatus of claim 4 wherein said apparatus comprises means for providing a first predetermined rate for adult patients and a second predetermined rate for neonate patients.

6. The apparatus of claim 1 wherein said trigger level establishing means comprises means for adding a predetermined threshold value to said baseline value to establish said trigger levels.

7. The apparatus of claim 6 wherein said apparatus comprises means for providing a first threshold value for patients with a deep respiration pattern and a second threshold value for patients with a shallow respiration pattern.

8. The apparatus of claim 1 wherein said selected crossovers only include crossovers by said respiration signal in the direction of a first polarity and not in the direction of a second polarity.

9. The apparatus of claim 8 wherein said inspiration trigger signal generating means comprises:
   means for inhibiting generation of inspiration trigger signals on first polarity crossovers in response to the presence of cardiovascular artifact and the suspected absence of inspiration.

10. The apparatus of claim 9 wherein said inhibiting means further comprises:
    means for disabling inhibition of said inspiration trigger signals when the heart rate of said patient is different from the respiration rate by more than a predetermined percentage.

11. The apparatus of claim 10 where said predetermined percentage is approximately 12.5%.

12. The apparatus of claim 8 wherein said inspiration trigger signal generating means comprises:
    means for inhibiting generation of inspiration signals on first polarity crossovers until said respiration signal remains at said first polarity following said crossover for a predetermined qualifying time.

13. The apparatus of claim 12 wherein said apparatus comprises means for providing a first predetermined qualifying time for adult patients and a second predetermined qualifying time for neonate patients.

14. A method for detecting inspiration of a patient in response to a time varying signal representative of the patient's respiration comprising the steps of:
    establishing a baseline level for said respiration signal which falls between the peak to peak variations of said respiration signal;
    establishing a trigger level for said respiration signal representative of inspiration;
    generating inspiration trigger signals in response to selected crossovers of said trigger level by said respiration signal;
    automatically detecting shifts in the baseline level of said respiration signal; and
    re-establishing said baseline and trigger levels in response to detection of said baseline shift.

15. The method of claim 14 wherein said step of detecting said shift comprises:
    detecting said baseline shifts within approximately one complete cycle of said respiration signal after said baseline shift has occurred.

16. The method of claim 14 wherein said step of detecting said baseline shift further comprises the steps of:
    establishing adjacent sector boundaries of opposite polarity for each cycle of said respiration waveform; and
    detecting when said waveform crosses a sector boundary of a first one of said polarities at least two times in succession without passing the sector boundary of the opposite polarity in between.

17. The method of claim 14 wherein the step of establishing said baseline level comprises the steps of:
    forming peak boundaries of opposite polarity for said respiration signals which peak boundaries start at each peak of said respiration signal and decay at a predetermined rate until said peak boundary intercepts said waveform before an adjacent peak of the same polarity; and
    establishing said baseline level at a level between said peak boundaries of opposite polarity.

18. The method of claim 17 wherein said method comprises providing a first predetermined rate for adult patients and a second predetermined rate for neonate patients.

19. The method of claim 14 wherein the step of establishing said trigger level comprises adding a predetermined threshold value to said baseline value to establish said trigger levels.

20. The method of claim 19 wherein said method comprises providing a first threshold value for patients with a deep respiration pattern and a second threshold value for patients with a shallow respiration pattern.

21. The method of claim 14 wherein said selected crossovers only include crossovers by said respiration signal in the direction of a first polarity and not in the direction of a second polarity.

22. The method of claim 21 wherein the step of generating said inspiration trigger signals further comprises the step of:
    inhibiting generation of inspiration trigger signals on first polarity crossovers in response to the presence of cardiovascular artifact and the suspected absence of inspiration.

23. The method of claim 22 wherein method further comprises the step of:
    disabling inhibition of said inspiration trigger signals when the heart rate of said patient is different from the respiration rate by more than a predetermined percentage.

24. The method of claim 23 where said predetermined percentage is approxmately 12.5%.

25. The apparatus of claim 21 wherein the step of generating said inspiration trigger signal comprises:
    inhibiting generation of inspiration signals on first polarity crossovers until said respiration signal remains at said first polarity following said crossover for a predetermined qualifying time.

26. The method of claim 25 wherein said method comprises providing a first predetermined qualifying time for adult patients and a second predetermined qualifying time for neonate patients.

* * * * *